(12) United States Patent
Turner

(10) Patent No.: US 10,646,637 B2
(45) Date of Patent: May 12, 2020

(54) CARDIOPLEGIC AGENT DELIVERY SYSTEM

(71) Applicant: Spectrum Medical Ltd., Gloucester (GB)

(72) Inventor: Stephen Turner, Gloucester (GB)

(73) Assignee: Spectrum Medical Ltd., Gloucester (GB)

( * ) Notice: Subject to any disclaimer, the term of this patent is extended or adjusted under 35 U.S.C. 154(b) by 271 days.

(21) Appl. No.: 15/526,613

(22) PCT Filed: Nov. 10, 2015

(86) PCT No.: PCT/GB2015/053404
§ 371 (c)(1),
(2) Date: May 12, 2017

(87) PCT Pub. No.: WO2016/075453
PCT Pub. Date: May 19, 2016

(65) Prior Publication Data
US 2017/0304523 A1    Oct. 26, 2017

(30) Foreign Application Priority Data
Nov. 13, 2014 (GB) .................................. 1420161.0

(51) Int. Cl.
*A61M 1/36* (2006.01)
*A61M 5/145* (2006.01)
(Continued)

(52) U.S. Cl.
CPC ........ *A61M 1/3664* (2013.01); *A61M 5/1452* (2013.01); *A61M 5/16827* (2013.01);
(Continued)

(58) Field of Classification Search
CPC ........ A61M 5/1452; A61M 2205/3334; A61M 2205/50; A61M 5/16827; A61M 5/16854; A61M 5/16877
See application file for complete search history.

(56) References Cited

U.S. PATENT DOCUMENTS

| 5,322,500 A | 6/1994 | Johnson et al. |
| 5,385,540 A | 1/1995 | Abbott et al. |
(Continued)

FOREIGN PATENT DOCUMENTS

| JP | H07-136275 A | 5/1995 |
| WO | WO 96/25972 | 8/1996 |
(Continued)

OTHER PUBLICATIONS

United Kingdom Intellectual Property Office, Search Report—Application No. GB1420161.0, dated May 7, 2015, 1 page.
(Continued)

*Primary Examiner* — Leslie R Deak
(74) *Attorney, Agent, or Firm* — Sunstein LLP

(57) ABSTRACT

A cardioplegic agent delivery system comprises a syringe pump for providing cardioplegic agent into a carrier fluid of a perfusion system, a flow sensor for sensing a flow of the carrier fluid, and an interlock responsive to the flow sensor. The interlock prevents operation of the syringe pump in the absence of carrier fluid flow sensed by the flow sensor. This provides increased safety in a cardioplegic agent delivery system.

15 Claims, 2 Drawing Sheets

(51) Int. Cl.
*A61M 5/168* (2006.01)
*A61M 5/172* (2006.01)

(52) U.S. Cl.
CPC ......... *A61M 5/172* (2013.01); *A61M 5/16854* (2013.01); *A61M 2205/276* (2013.01); *A61M 2205/3334* (2013.01); *A61M 2205/3344* (2013.01); *A61M 2205/3368* (2013.01); *A61M 2205/50* (2013.01)

(56) References Cited

U.S. PATENT DOCUMENTS 5,573,502 A    11/1996   Lecocq et al.
5,573,505 A    11/1996   Johnson et al.

FOREIGN PATENT DOCUMENTS

| WO | WO 96/39211 | 12/1996 |
| WO | WO 99/32172 | 7/1999 |
| WO | WO 2012/011115 | 1/2012 |

OTHER PUBLICATIONS

S. Dimantouros, Authorized officer European Patent Office, International Search Report—Application No. PCT/GB2015/053404, dated Jan. 25, 2016, together with the Written Opinion of the International Searching Authority, 8 pages.
Chinese Patent Office; Office action dated Jun. 28, 2019 dated for Chinese patent application No. 2015800622411, 14 pp.
Japanese Patent Office; Office action dated Jul. 9, 2019 for Japanese patent application No. 2017-526589, 7 pp.
European Patent Office, Examination Report for European application No. 15794274.9, dated Jan. 30, 2020, 4 pages.

CARDIOPLEGIC AGENT DELIVERY SYSTEM

FIELD OF THE INVENTION

The present invention relates to a device for use in cardioplegia management, specifically for use in cardioplegia management during surgery. More specifically, the present invention relates to a device for delivering a cardioplegic solution, and to a method of preparing a cardioplegic solution for administration.

BACKGROUND OF THE INVENTION

During surgery on the heart, such as cardiac bypass surgery, surgeons stop the heart to enable them to operate on a still heart. The heart can be stopped by administering a cardioplegic solution to the heart tissue. A cardioplegic solution contains ions, typically potassium ions ($K^+$), that can interfere with the metabolism, or physiological stimulation, of muscle cells if supplied at a concentration high enough and, thus, allow heartbeat to be suppressed. While the heart is stopped, a heart-lung machine (HLM) is used to maintain a supply of oxygen to the patient to keep the patient alive during surgery. A HLM comprises a perfusion circuit in which venous blood is drawn from a patient, oxygenated, and administered arterially to a patient. For the administration of cardioplegic solution, a portion of blood is drawn from the (principal) perfusion circuit of the HLM into a secondary circuit (conveniently, after oxygenation), infused with cardioplegic solution, and administered to the heart. The concentration of the cardioplegic solution must be carefully controlled within narrow margins. If the concentration of the cardioplegic solution is too low, the suppressive effect may cease early and a heart may unexpectedly beat during surgery. Too high a concentration of the cardioplegic solution can be lethal.

The present invention seeks to provide an improved solution for cardioplegia management.

SUMMARY OF THE INVENTION

In accordance with a first aspect of the present invention, there is described a cardioplegic agent delivery system as defined in claim 1.

The cardioplegic agent delivery system comprises a syringe pump for providing cardioplegic agent into a carrier fluid of a perfusion system; a flow sensor for sensing a flow of the carrier fluid; and an interlock responsive to the flow sensor, the interlock preventing operation of the syringe pump to provide cardioplegic agent into the carrier fluid in the absence of flow sensed by the flow sensor.

In one embodiment, the carrier fluid is a liquid, in particular a physiological liquid such as blood or a blood substitute, suitable for administration into the heart. For instance, the carrier fluid may be blood drawn from a perfusion circuit during heart surgery.

The cardioplegic agent may be provided as a solution of predetermined concentration.

Because the effect of cardioplegic agent on the heart wears off over time, it is normal to re-supply cardioplegic agent, as required, to maintain the heart in a paralysed, or suppressed, condition. In practice, blood may be drawn from the perfusion circuit, at regular intervals of, for instance, 20 minutes, re-supplied with cardioplegic agent and fed back into the heart in order to maintain a suppressive effect. This is repeated continually throughout the period a still heart is required.

The administration of cardioplegic solution is the responsibility of trained professionals (perfusionists). Under current procedures, the perfusionist would monitor heart activity parameters via an ECG monitor and determine whether or not cardioplegic solution must be administered in order to maintain the heart still, and would administer a cardioplegic solution manually, or actuate a syringe pump manually, as and when required.

A problem with the prior art is that there is a risk if blood circulation in the cardioplegic perfusion circuit has to be temporarily stopped, for instance, while a vessel or heart chamber is opened during surgery. In such a case, a dose of cardioplegic solution may be injected into carrier fluid taken from the perfusion circuit just before, or while, the blood circulation is stopped. This risks that the cardioplegic solution remains within the portion of the circuit into which it was injected and that it does not reach the heart. Furthermore, this can lead to a locally increased concentration of cardioplegic solution in a portion of blood that will reach the heart once blood circulation is restarted. If that portion reaches the heart, this can have adverse consequences due to a stronger suppressive effect on the heart.

It is an advantage of the present invention that a flow sensor is provided that triggers an interlock to allow the syringe pump to be operated only when there is a flow of the carrier fluid. Thereby, the administration of cardioplegic agent into the carrier fluid can be coordinated with a flow of the carrier fluid. Because the syringe pump operation is interlocked with the flow of the carrier fluid such that the syringe pump will feed cardioplegic agent only if the carrier fluid is flowing, the risk of a localised build-up of cardioplegic agent in a stagnant portion of carrier fluid is eliminated (or at least significantly reduced).

The syringe pump is a device permitting controlled delivery of predetermined volumes of the cardioplegic agent into the carrier fluid. The controlled delivery may include feeding the cardioplegic agent at a pre-determined peak flow rate, or at a pre-determined average flow rate.

It is understood that a "syringe pump" is a positive displacement pump comprising a displacing element to act on a fluid container, such as a plunger-in-barrel type arrangement. The fluid container comprises an outlet port to be connected to a feeding port for receiving a substance from the fluid container. The displaceable element is movable to displace a substance in the container towards the outlet port.

By "controlled delivery", it is meant that the displacing element of a syringe pump can be driven with high precision to allow small volumes of a substance, e.g. of cardioplegic agent, to be dispensed through the outlet port. For instance, a stepper motor may drive the displacing element with micrometre precision to allow microliter volumes to be dispensed.

The cardioplegic agent may be supplied in a replaceable cartridge, a refillable cartridge, or as a disposable container.

It will be appreciated that, in operation, the syringe pump will be configured to feed cardioplegic agent via a feeding port into carrier fluid in the perfusion system (which may be a secondary perfusion circuit). A flow of carrier fluid will lead from an inlet upstream of the feeding port past the feeding port and further to an outlet downstream of the feeding port.

The flow sensor may be positioned close to the feeding port from the syringe pump, either upstream or downstream. The flow sensor may be configured for contactless flow measurement, for instance by using acoustic or optical Doppler flow velocimetry. This avoids contamination and reduces maintenance requirements.

The flow sensor may be remote from the syringe pump. For instance, the flow sensor may be positioned at the inlet of the secondary perfusion circuit, or at the outlet of the secondary perfusion circuit, or upstream or downstream of the pump generating flow of the carrier liquid. This allows the flow sensor to be positioned where this is most suitable to provide a reliable flow measurement. The data connection between the flow sensor and the syringe pump may be wireless. The data connection between the flow sensor and the syringe pump may be wired.

Hitherto, syringe pumps for feeding cardioplegic agent that were installed to a perfusion system were operative to dispense cardioplegic agent into the perfusion system independently of any flow in the perfusion system. The interlock with a flow sensor provided by the present invention reduces reliance on inputs of external system parameters or on manual activation. As such, the syringe pump of the present cardioplegic agent delivery system increases patient safety.

In an embodiment, the interlock is configured to control actuation of the syringe pump to feed cardioplegic agent into the carrier fluid only when the flow rate of the carrier fluid exceeds a predetermined threshold.

The controller may be configured to activate the syringe pump to feed cardioplegic agent in to the carrier fluid while, or only while, the flow of the carrier fluid exceeds as predetermined threshold.

It is an advantage if the cardioplegic agent is supplied while the carrier fluid circulates above a pre-determined flow rate threshold, as this helps ensuring that the cardioplegic agent is not fed at flow conditions that make accurate dosing difficult. For instance, at very low carrier fluid flow rates, the dose of cardioplegic agent may have to be correspondingly small, increasing the impact of dosing inaccuracies. Likewise, operating the feeder arrangement only above a pre-determined flow rate practically eliminates the possibility of mixing the cardioplegic agent into the carrier fluid while this is stagnant, which could lead to a locally (locally in the carrier fluid stream) high concentration, or "burst", of cardioplegic agent, which may be unsafe to administer.

Thus, operating the feeder arrangement only above a pre-determined flow rate reduces the risk of localised unsafely high concentrations of cardioplegic agent that might otherwise accumulate locally if the carrier fluid is circulated only intermittently.

This means that when the cardioplegic agent is fed into the carrier fluid, it is sufficiently diluted in the carrier fluid to avoid a locally concentrated portion of cardioplegic solution in the blood stream.

In an embodiment, the cardioplegic agent delivery system further comprises a controller for controlling the syringe pump, wherein the flow sensor is configured to obtain a signal indicative of the flow rate of the carrier fluid in the perfusion circuit for interpretation by the controller, and wherein the controller is configured to actuate the syringe pump in response to the signal.

In an embodiment, the controller comprises a processor and software instructions implemented by the processor, and wherein the interlock comprises instructions implemented by the processor.

In an embodiment, the controller is configured to adjust the delivery rate of cardioplegic agent from the syringe pump into the carrier fluid according to the flow rate of the carrier fluid.

The feeding rate of cardioplegic agent may be adjusted to the flow rate of the carrier fluid. For instance, if a higher flow rate of the carrier fluid is measured, the syringe pump may be instructed to feed cardioplegic agent at a correspondingly higher rate. Vice versa, the cardioplegic agent may be fed at a lower rate if the carrier fluid flow rate is low. Also, the amount of cardioplegic agent to be fed may depend on the concentration of the cardioplegic agent in solution. The amount of cardioplegic agent fed into the carrier fluid may be adjusted so that a desired concentration of cardioplegic agent is achieved in the carrier fluid before it is pumped to a heart.

In an embodiment, the delivery system further comprises a cardioplegia circuit pump to generate a flow between an inlet of the system and an outlet of the system.

The cardioplegia circuit pump is a pump suitable for pumping a volume of carrier fluid from a main perfusion circuit. For instance, the cardioplegia circuit pump may be used to draw blood from a principal perfusion circuit in order to generate a flow in the cardioplegia circuit when it is desired to supply cardioplegic agent to a patient. In this context, when the present specification refers to a delivery system, this may comprise or be connected to a cardioplegia circuit, whose inlet is be supplied from the primary perfusion circuit, and whose outlet may be further connected to a heart.

A cardioplegia circuit pump comprised with the delivery system facilitates a configuration allowing the controller to interpret control signals issued to the cardioplegia circuit pump. The controller may be configured to modulate actuation of the syringe pump in response to the control signals.

The interlock may be able to derive, e.g. by the controller, from the control signals for which period of time the cardioplegia circuit pump is generating flow. The interlock may be configured to make a determination as to whether or not a control signal that has been provided to the cardioplegia circuit pump is sufficient to generate flow to deliver cardioplegic agent with the carrier fluid out through the outlet. The syringe pump may be activated to feed the cardioplegic agent into the carrier fluid only if such a control signal is sufficient. The controller may be configured to derive the length of a cardioplegia circuit pump cycle and to feed cardioplegic agent during an early phase of the pump cycle, to ensure flow of carrier fluid after the cardioplegic agent has been fed into the carrier fluid. The early phase may be constituted by the first ⅔, ½, or ⅓ of a pump cycle.

Activating the syringe pump only when the cardioplegia circuit pump is instructed to generate flow helps to ensure that the cardioplegic agent that is fed into the carrier fluid is also delivered through the outlet, e.g. to a heart.

In an embodiment, the delivery system is configured to ensure operation of the cardioplegia circuit pump for a predetermined period of time after cardioplegic agent has been fed into the carrier fluid.

It is understood that the predetermined amount of time is dependent on factors such as the length of the perfusion lines and the flow rate of the carrier fluid.

It is an advantage if the controller logic can derive how much cardioplegic agent is to be fed into the carrier fluid during the early phase of its circulation. It is undesirable that a cardioplegia circuit pump continues pumping until after a stop signal has been sent, because a surgeon may have to rely on blood circulation having stopped in order to perform surgery on a particular organ.

It is an advantage that, by way of the establishing the period of time during which the cardioplegia circuit pump continues to circulate the carrier fluid, it can be ensured that the cardioplegia circuit pump continues pumping after the cardioplegic agent has been fed. This reduces the occurrence of cardioplegic agent remaining in the carrier fluid syringe pump and a patient when circulation is stopped. This also helps ensuring that all cardioplegic agent that is fed into the carrier fluid reaches the heart.

In an embodiment, the flow sensor is configured to measure the flow rate of the carrier fluid downstream of the syringe pump.

The provision of a flow meter downstream of the syringe pump, or downstream of the feeding port of the syringe pump, allows the actual flow rate of the carrier fluid with the cardioplegic agent to be determined.

If, for any reason, the flow rate is not consistent with values that would be expected from the cardioplegia circuit pump under normal operating conditions, countermeasures can be taken. In determining the flow rate, any influence of the syringe pump on the flow rate may be taken into account. For instance, the delivery system may determine a difference between the actual flow rate and an expected flow rate. If any difference is within a safety margin, the delivery system may continue to operate as normal. If any difference is outside a safety margin, the delivery system may issue an alert notification. Also, some wear of the cardioplegia circuit pump, or loss of pump efficiency, may be expected under normal conditions, and this can be counteracted by adjusting the speed of the cardioplegia circuit pump. Thus, measuring the actual carrier fluid flow rate provides a means of better or more safely utilising the cardioplegia circuit pump.

Embodiments of the syringe pump may comprise a temperature sensor to obtain temperature parameters indicative of the temperature of the carrier fluid for interpretation by the controller. The controller may be configured to control syringe pump actuation in response to the temperature parameters.

Embodiments of the syringe pump may comprise a pressure sensor to obtain pressure parameters indicative of the pressure of the carrier fluid for interpretation by the controller. The controller may be configured to control syringe pump actuation in response to the pressure parameters.

Embodiments of the syringe pump may comprise a sensor capable of obtaining cardioplegic parameters indicative of the concentration of cardioplegic agent in the carrier fluid for interpretation by the controller. The controller may be configured to control syringe pump actuation in response to the cardioplegic parameters.

The provision of sensors with the syringe pump facilitates the installation and calibration of the sensors in relation to signals or parameters required to determine the actuation of the syringe pump. The sensors may be connected to the syringe pump or to the syringe pump controller via dedicated connection or channel. By "dedicated", it is meant that the connection or channel is used exclusively by the syringe pump. This avoids interference with other sensors of the perfusion circuit.

Consideration of these parameters allows the feeding rate of the syringe pump to be modulated with higher accuracy.

According to a second aspect of the present invention, there is provided a syringe pump as defined in claim 10. Embodiments of the second aspects may comprise, in any combination, features of the first aspect. For instance, embodiments of the second aspect may comprise a flow sensor, a temperature sensor, a pressure sensor, a sensor to determine the concentration of cardioplegic agent, or combinations of these. A controller of the syringe pump may be configured to modulate dispensing of cardioplegic agent in response to the signals.

According to a third aspect of the present invention, there is provided a method of controlling a delivery system to prepare a cardioplegic solution as defined in claim 15.

The method provides for controlling a cardioplegic agent delivery system to prepare a cardioplegic solution, wherein the delivery system comprises a syringe pump for providing cardioplegic agent into a carrier fluid, and further comprises a flow sensor and an interlock responsive to the flow sensor. The method comprises the steps of using the flow sensor to sense a flow of the carrier fluid, and operating the interlock to allow operation of the syringe pump when the flow sensor senses flow of the carrier fluid, and to prevent the syringe pump from delivering cardioplegic agent into the carrier fluid in the absence of flow sensed by the flow sensor.

BRIEF DESCRIPTION OF THE FIGURE

Specific exemplary embodiments of the invention are now described with reference to FIG. 1, which shows a schematic arrangement of components of a delivery system of the present invention.

DETAILED DESCRIPTION

Figure 1:
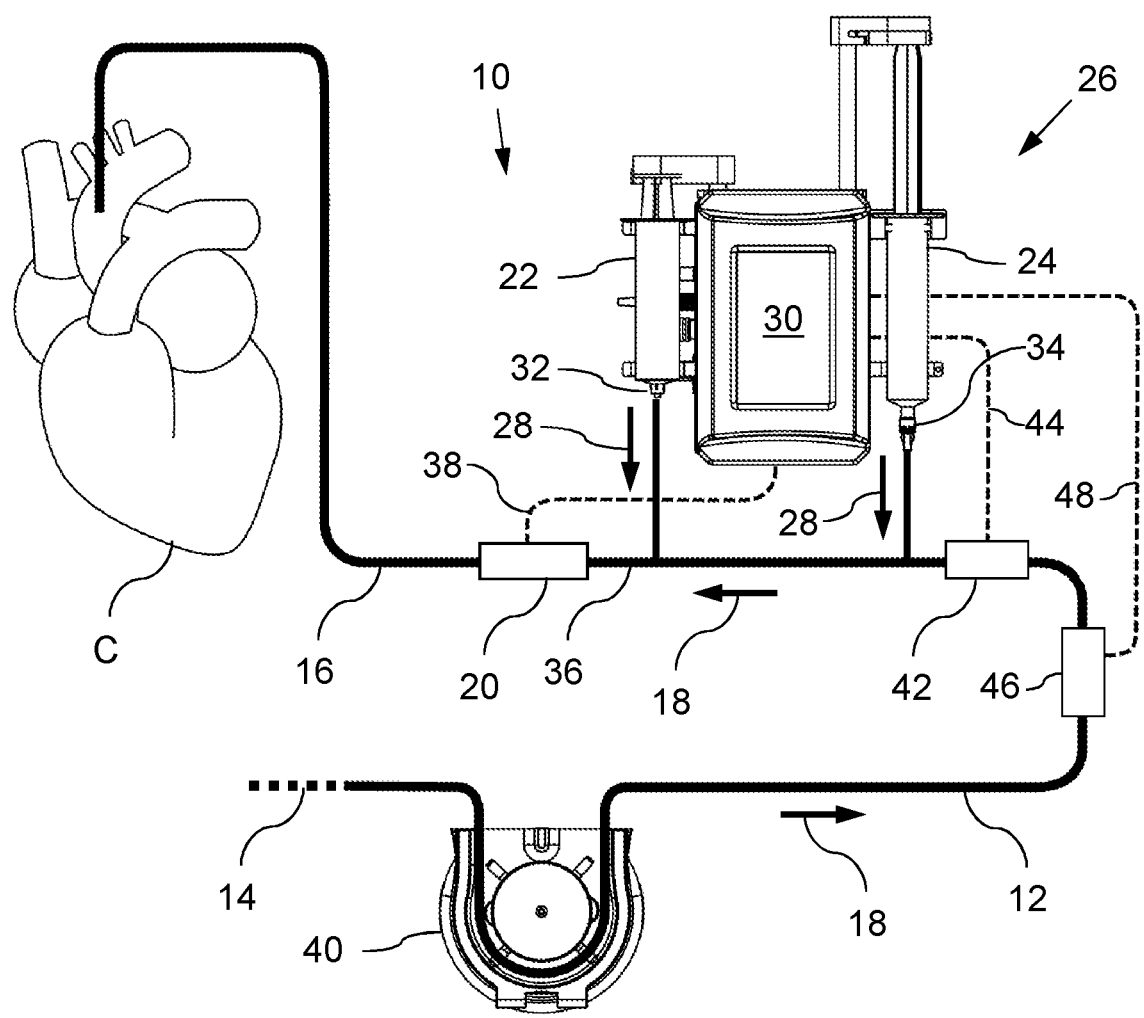

FIG. 1 shows a delivery system 10 for delivering a cardioplegic agent. The delivery system 10 is integrated with a cardioplegia circuit 12. The cardioplegia circuit 12 draws oxygenated blood (constituting a carrier fluid) from a perfusion circuit of a heart-lung machine (not shown in FIG. 1) via an inlet 14. From the inlet 14 the carrier fluid circulates in the direction indicated by arrows 18 towards outlet 16, through which the carrier fluid is pumped away. As shown in FIG. 1, the outlet 16 is to be further connected to a heart C.

The delivery system 10 comprises a flow sensor 20 connected via a data channel 38 to a controller 30. Data channel 38 may be wireless. Data channel 38 may be wired. The flow sensor 20 is configured to obtain data about or indicative of the flow of the carrier fluid in the cardioplegia circuit 12. Measurements obtained by flow sensor 20 are fed back via the data channel 38 to the controller 30.

The delivery system 10 comprises a syringe pump arrangement 26, shown in FIG. 1 as comprising two syringe pumps 22, 24, each operated by a stepper motor controlled by controller 30. In FIG. 1, controller 30 is shown as integral with a syringe pump arrangement 26, but it will be appreciated that controller 30 may be located elsewhere.

The syringe pumps 22, 24 can be operated, via the controller 30, to feed in the direction of arrows 28 a cardioplegic agent into the carrier fluid via feeding ports 32 or 34, respectively.

Based on whether or not the flow rate, as measured by the flow sensor 20, is above a threshold value, the controller 30 issues control signals preventing the actuation of either or both of syringe pump 22 or syringe pump 24. Thereby, it can be ensured that cardioplegic solution is fed into the carrier fluid only if there is a sufficiently high flow rate of the carrier fluid. Thereby, the syringe pumps are interlocked with the flow of the carrier fluid. Even though the present FIG. 1 embodiment is described as comprising a controller, the interlock may be implemented by another mechanism, e.g., by allowing the flow sensor 20 to block operation of the syringe pump arrangement 26 directly.

If a cardioplegic agent is fed into the carrier fluid, the concentration of cardioplegic agent will be higher downstream of the feeding ports 32 or 34, in a region indicated by numeral 36 in FIG. 1. In the embodiment of FIG. 1, the flow sensor 20 is located downstream of the feeding ports 32 and 34.

Also shown in FIG. 1 is a cardioplegia circuit pump 40 which is provided to circulate the carrier fluid in the cardioplegia circuit 12. In some embodiments, the cardioplegia circuit pump 40 is comprised with the delivery system 10. In such embodiments, the controller 30 may have access to operating parameters of the cardioplegia circuit pump 40. In some embodiments, the cardioplegia circuit pump 40 is not comprised with the delivery system. This possibility is enabled by the present invention, because the interlock between the syringe pump arrangement 26 and the flow sensor 20 provides independence of the flow-generating means in the cardioplegia circuit 12. However, if a circuit pump 40 is comprised in the delivery system, this allows additional functionality to be integrated.

By way of data obtained from the flow sensor 20, the controller 30 can control the operation of the syringe pumps 22 and 24 and thereby interlock the feed of cardioplegic agent with operation of the cardioplegia circuit pump 40. The activation pattern of syringe pumps 22 and 24 can be altered in response to parameters derived from the pump activity and/or flow rate.

For instance, if cardioplegia circuit pump 40 is not circulating the carrier fluid at a suitable rate, the syringe pumps 22 and 24 may not be activated by the controller 30. Likewise, if the control signals indicate that the carrier fluid will be circulated only for a particular length of time, the controller 30 may instruct the syringe pumps 22 and 24 to feed cardioplegic agent only for a proportion of the particular length of time, to ensure that the cardioplegic agent fed can subsequently reach the heart C.

This helps preventing an increase of cardioplegic agent in the region 36 and thereby prevents an undesired dose of cardioplegic agent from being delivered to a patient upon subsequent activation of the pump.

In the embodiment shown in FIG. 1, the syringe pump arrangement 26 comprises a pressure sensor 42. The pressure sensor 42 allows the pressure of the blood in the cardioplegia circuit 12 to be determined. The pressure sensor 42 is connected to the syringe pump arrangement 26 via a data channel 44. The data channel 44 may be wireless. The data channel 44 may be wired.

In the embodiment shown in FIG. 1, the syringe pump arrangement 26 comprises a temperature sensor 46. The temperature sensor 46 allows the temperature of the blood in the cardioplegia circuit 12 to be determined. The temperature sensor 46 is connected to the syringe pump arrangement 26 via a data channel 48. The data channel 48 may be wireless. The data channel 48 may be wired.

In embodiments comprising a pressure sensor 42, a temperature sensor 46, or both, the data channel 44 and/or 46 may be connected directly to the controller 30 of the syringe pump arrangement 26. As indicated in FIG. 1, the data channels 38, 44 and 48 are dedicated data channels not shared with other components of the perfusion circuit, and as such exclusive to the syringe pump. This avoids problems with interference or bandwidth.

In the embodiment shown in FIG. 1, the cardioplegia circuit pump 40 is a peristaltic, or "roller", pump permitting the generation of flow without contamination risk. Other pump types may be used.

Although two syringe pumps 22, 24 and two feeding ports 32, 34 are depicted in FIG. 1, other arrangements may be used, such as a single syringe pump. A dual syringe pump arrangement has the advantage that one of the two syringe pumps may be refilled, or exchanged, while the other of the two syringe pumps remains operative. Alternatively or concurrently, multiple syringe pumps may be used to supply cardioplegic agent at different concentrations, e.g., a lower concentration to be administered at a low flow rate of carrier fluid, and a higher concentration to be administered at a high flow rate of carrier fluid. This helps improving an appropriate dosage.

The controller 30 may process parameters other than the flow rate provided by the flow sensor 20. In embodiments comprising a pressure sensor 42 and/or a temperature sensor 46, the controller 30 is enabled to process the pressure and/or temperature. For instance, an input may be obtained from another sensor within the system, such as a cardioplegia circuit pump if this is not a component of the delivery system 10. It is contemplated that the parameters controlling the interlock are to be set up via a software interface. For instance, the length of the perfusion line between the feeding port and the heart may be entered as a parameter in order for this to be considered in the determination as to in which time window to feed cardioplegic agent.

Furthermore, the arrangement shown in FIG. 1 allows parameters other than the flow rate to be considered. For instance, for the actuation of the feeder arrangement, parameters, such as temperature, pressure values, or the concentration of a biomarker, may be taken into account, or whether such parameters fall below, or rise above, a predetermined threshold.

Figure 2:
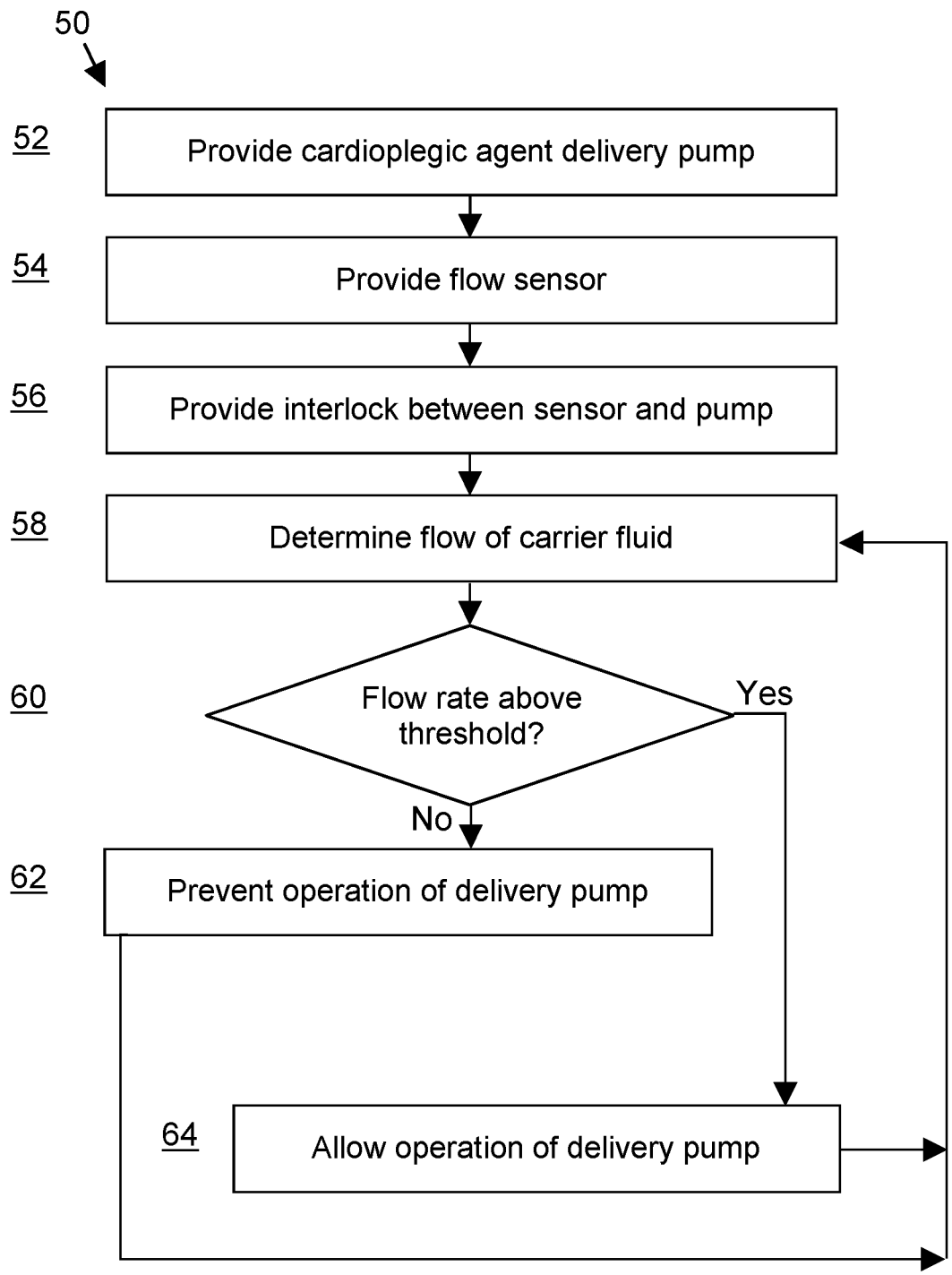
FIG. 2 is a flow chart of steps of the method of controlling a cardioplegic agent delivery system.

FIG. 2 shows steps of a method 50 of controlling a cardioplegic agent delivery system to prepare a cardioplegic solution. In step 52, a cardioplegic agent delivery pump is provided. The delivery pump allows cardioplegic agent to be delivered into a carrier fluid. In step 54, a flow sensor is provided. The flow sensor is capable of measuring the flow of the carrier fluid. In step 56, an interlock is established between the flow sensor and the delivery pump. I.e., the interlock is responsive to the flow sensor. In step 58, the flow sensor measures the flow rate. In step 60, a determination is made whether the flow rate of the carrier fluid is above a threshold, i.e., whether or not there is any flow, or sufficient flow, of the carrier fluid. In step 62, in the absence of flow or sufficient flow, operation of the delivery pump is prevented, to prevent injection of cardioplegic agent into the carrier fluid. In step 64, if there is flow or sufficient flow, operation of the delivery pump is permitted.

The invention claimed is:

1. A cardioplegic agent delivery system comprising:
    a syringe pump for providing cardioplegic agent into a carrier fluid of a perfusion system;
    a flow sensor for sensing a flow rate of the carrier fluid; and
    an interlock responsive to the flow sensor, the interlock preventing operation of the syringe pump to provide cardioplegic agent into the carrier fluid in the absence of flow sensed by the flow sensor, wherein the interlock is programmed to control actuation of the syringe pump to feed cardioplegic agent into the carrier fluid only when the flow rate of the carrier fluid exceeds a predetermined threshold.

2. The cardioplegic agent delivery system according to claim 1, wherein the interlock is implemented by a controller for controlling the syringe pump, wherein the flow sensor is configured to obtain a signal indicative of the flow rate of the carrier fluid for interpretation by the controller, and wherein the controller is configured to actuate the syringe pump in response to the signal.

3. The cardioplegic agent delivery system according to claim 2, wherein the controller comprises a processor and software instructions implemented by the processor, and wherein the interlock comprises instructions implemented by the processor.

4. The cardioplegic agent delivery system according to claim 1, further comprising a cardioplegia circuit pump to generate a flow between an inlet of the system and an outlet of the system.

5. The cardioplegic agent delivery system according to claim 4, programmed to ensure operation of the cardioplegia circuit pump for a predetermined period of time after cardioplegic agent has been fed into the carrier fluid.

6. The cardioplegic agent delivery system according to claim 1, wherein the flow sensor is configured to measure the flow rate of the carrier fluid downstream of the syringe pump.

7. The cardioplegic agent delivery system according to claim 1, wherein the syringe pump further comprises a temperature sensor to obtain temperature parameters indicative of a temperature of the carrier fluid for interpretation by the controller, and wherein the controller is configured to control syringe pump actuation in response to the temperature parameters.

8. The cardioplegic agent delivery system according to claim 1, wherein the syringe pump further comprises a pressure sensor to obtain pressure parameters indicative of a pressure of the carrier fluid for interpretation by the controller, and wherein the controller is configured to control syringe pump actuation in response to the pressure parameters.

9. The cardioplegic agent delivery system according to claim 1, wherein the syringe pump further comprises a sensor capable of obtaining cardioplegic parameters indicative of a concentration of cardioplegic agent in the carrier fluid for interpretation by the controller, and wherein the controller is configured to control syringe pump actuation in response to the cardioplegic parameters.

10. A syringe pump for use in a cardioplegia circuit, the syringe pump comprising
    a reservoir containing a cardioplegic agent;
    an actuator for dispensing the cardioplegic agent into a carrier fluid of the cardioplegia circuit; and
    a controller to control the actuator, wherein the controller is programmed to receive a signal indicative of a flow rate of the carrier fluid and to dispense cardioplegic agent only if the flow rate exceeds a predetermined threshold.

11. The syringe pump according to claim 10, further comprising a flow sensor to obtain a signal indicative of the flow rate of the carrier fluid.

12. The syringe pump according to claim 10, further comprising a temperature sensor to obtain a temperature signal indicative of a temperature of the carrier fluid, and wherein the controller is configured to modulate dispensing of the cardioplegic agent in response to the temperature signal.

13. The syringe pump according to claim 10, further comprising a pressure sensor to obtain a pressure signal indicative of a pressure of the carrier fluid, and wherein the controller is programmed to modulate dispensing of the cardioplegic agent in response to the pressure signal.

14. The syringe pump according to claim 10, further comprising a sensor to obtain a cardioplegic signal indicative of a concentration of cardioplegic agent in the carrier fluid, and wherein the controller is programmed to modulate dispensing of the cardioplegic agent in response to the cardioplegic signal.

15. A method of controlling a cardioplegic agent delivery system to prepare a cardioplegic solution, wherein the delivery system comprises a syringe pump for providing cardioplegic agent into a carrier fluid, and further comprises a flow sensor and an interlock responsive to the flow sensor, and wherein the method comprises the steps of:
    using the flow sensor to sense a flow rate of the carrier fluid, and
    operating the interlock to allow operation of the syringe pump when the flow sensor senses flow of the carrier fluid, and to prevent the syringe pump from delivering cardioplegic agent into the carrier fluid in the absence of flow sensed by the flow sensor.

* * * * *